(12) United States Patent
Beecroft et al.

(10) Patent No.: US 9,555,414 B2
(45) Date of Patent: Jan. 31, 2017

(54) VIAL RACK FOR LIQUID CHROMATOGRAPHY HAVING DRAINING MEANS

(71) Applicant: EURO-CELTIQUE S.A., Luxembourg (LU)

(72) Inventors: Ross Oliver Beecroft, Cambridgeshire (GB); Victoria Louise Goff, Cambridgeshire (GB); Sarah Jane Karim, Cambridgeshire (GB); Nicholas Brian Milne, Cambridgeshire (GB)

(73) Assignee: EURO-CELTIQUE S.A., Luxembourg (LU)

( * ) Notice: Subject to any disclaimer, the term of this patent is extended or adjusted under 35 U.S.C. 154(b) by 92 days.

(21) Appl. No.: 14/364,986

(22) PCT Filed: Dec. 14, 2012

(86) PCT No.: PCT/GB2012/053149
§ 371 (c)(1),
(2) Date: Jun. 12, 2014

(87) PCT Pub. No.: WO2013/088171
PCT Pub. Date: Jun. 20, 2013

(65) Prior Publication Data
US 2014/0377878 A1   Dec. 25, 2014

(30) Foreign Application Priority Data
Dec. 14, 2011 (GB) .................................... 1121504.3

(51) Int. Cl.
*G01N 30/02* (2006.01)
*B01L 9/06* (2006.01)
*G01N 30/24* (2006.01)

(52) U.S. Cl.
CPC *B01L 9/06* (2013.01); *G01N 30/24* (2013.01)

(58) Field of Classification Search
None
See application file for complete search history.

(56) References Cited

U.S. PATENT DOCUMENTS

| 4,862,932 A | 9/1989 | Feinstein |
| 5,291,997 A | 3/1994 | He et al. |
| 5,738,827 A | 4/1998 | Marquiss |
| 2005/0207941 A1 | 9/2005 | Lee et al. |

FOREIGN PATENT DOCUMENTS

EP   0 338 692   10/1989

OTHER PUBLICATIONS

International Preliminary Report on Patentability dated Jun. 17, 2014, issued in corresponding International Application No. PCT/GB2012/053149.
International Search Report for PCT/GB2012/053149, mailed Mar. 4, 2013, Skowronski, Maik.
Written Opinion of the International Searching Authority for PCT/GB2012/053149, mailed Mar. 4, 2013, Skowronski, Maik.

*Primary Examiner* — Robert Xu
(74) *Attorney, Agent, or Firm* — Nixon & Vanderhye P.C.

(57) ABSTRACT

The present invention provides a rack for holding sample vials comprising: (i) a solid base; (ii) an upwardly extending wall around the perimeter of said base; (iii) a plurality of means for supporting a plurality of vials, each means for supporting one vial; and (iv) a means for draining liquid from said rack.

31 Claims, 9 Drawing Sheets

VIAL RACK FOR LIQUID CHROMATOGRAPHY HAVING DRAINING MEANS

This application is the U.S. national phase of International Application No. PCT/GB2012/053149, filed on Dec. 14, 2012, which designated the U.S. and claims priority to GB Application No. 1121504.3, filed on Dec. 14, 2011, the entire contents of each of which are incorporated herein by reference.

FIELD OF THE INVENTION

The present invention relates to a rack for holding sample vials for use in a sampling arrangement for a liquid chromatography device. The invention also relates to the sampling arrangement per se and to the liquid chromatography apparatus comprising the sampling arrangement per se. The invention further relates to a method for analysing an analyte present in a liquid at a plurality of time points over a period of time.

BACKGROUND

Ultra high performance liquid chromatography (UHPLC) has developed over the last decade in response to the need for faster chromatography techniques that can handle the vast number of samples generated during drug discovery and development. Compared to HPLC, which has been the predominant technology used in laboratories across a wide range of technical fields, UHPLC is carried out with columns comprising particles of a smaller size and increased mobile phase flow rates. Typically the particles present in UHPLC columns will be less than 2 μm in size, e.g. 1.7 to 1.8 μm, and typically a pressure of 50-100 MPa is used to achieve high throughput. The effect of the smaller particles is to ensure analytes are still separated in the column despite their shorter residence time therein.

UHPLC is used to monitor the progress of chemical reactions, as well as physical or other transformations, e.g. dissolution studies, in a wide range of different contexts. Reactions may, for instance, be monitored by analysing the depletion of a starting material or the generation of a product. UHPLC is, however, particularly useful during drug development wherein huge numbers of reactions take place. During drug development, UHPLC may be used to monitor the progress of reactions during chemical syntheses, to monitor the stability of compounds to different conditions and to monitor the pharmacokinetic properties of drugs and their formulations. During the formulation stage of drug development, for example, UHPLC may be used to assess the properties of different formulations, e.g. dissolution rates in a variety of different conditions. For instance, a range of pharmaceutical formulations may be prepared with varying amounts of a set of excipients and/or varying excipients and the dissolution rates of each of the formulations determined. This is carried out by placing each formulation in a dissolution media and then monitoring the media for the presence of the drug. The monitoring is carried out by removing a sample of the liquid at regular intervals and analysing it by UHPLC to determine the amount of drug present therein. The data gathered, usually in replicate, from the different time points can then be used to generate an average dissolution curve.

In a conventional UHPLC set up a rack for holding sample-containing vials is provided on a shuttle tray which is positioned in the UHPLC analyser wherein an aliquot of sample is taken from a first vial and analysed. The UHPLC analyser will then take an aliquot of sample from another vial in the array and analyse it. This process is repeated until a sample is taken from each vial and is analysed.

Typically, however, the manner of collecting and analysing samples from multiple vessels is very intensive, particularly if replicates of each sample are to be analysed. This burden is further exacerbated in the case of monitoring chemical reactions, physical or other transformations (hereinafter referred to collectively as "reaction monitoring" or "monitoring of reactions"), e.g. dissolution studies, wherein there is a need for the analysis to be repeated at a number of different points in time. Overall it means there is a need to collect a vast number of samples into vials and for these to be transported reliably and efficiently to the UHPLC analyser for analysis.

One way in which this problem has been overcome is to carry out the reaction, test or study, e.g. dissolution study, to be monitored in sample vials within a liquid chromatography device. This solution is, however, very limited. It is often not possible to set up reactions, tests or studies under the necessary conditions within the confines of a liquid chromatography device, e.g. it is not possible to provide any heating or cooling to the reaction, test or study within the device. It is also not possible to carry out reactions, tests or studies at anything other than a very small scale. Thus, for example, it is not possible to monitor the dissolution rates of many tablet formulations since the capacity of even the largest sample vials is too small to contain the required amount of dissolution media.

A need therefore still exists for improved equipment and methods for automated and continuous monitoring of reactions.

SUMMARY OF THE INVENTION

Thus viewed from a first aspect, the present invention provides a rack for holding sample vials comprising:
(i) a solid base;
(ii) an upwardly extending wall around the perimeter of said base;
(iii) a plurality of means for supporting a plurality of vials, each means for supporting one vial; and
(iv) a means for draining liquid from said rack.

Viewed from a further aspect, the present invention provides a sampling arrangement for a liquid chromatography device comprising:
(i) a rack as hereinbefore defined.

Viewed from a further aspect, the present invention provides a liquid chromatography apparatus comprising:
(i) a sampling arrangement as hereinbefore defined; and
(ii) a liquid chromatography device.

Viewed from a still further aspect, the present invention provides a method for analysing an analyte present in a liquid to be sampled at a plurality of time points over a period of time comprising:
(i) providing a supply of sample of said liquid to a sampling arrangement as hereinbefore defined;
(ii) removing an aliquot of sample from said arrangement at selected time points;
(iii) injecting said aliquot of said sample into a liquid chromatography device; and
(iv) analysing said analyte.

Viewed from a further aspect, the present invention provides the use of a rack as hereinbefore described in a sampling arrangement for a liquid chromatography device.

Viewed from a further aspect, the present invention provides use of a sampling arrangement as hereinbefore defined in a liquid chromatography apparatus.

Viewed from a further aspect, the present invention provides use of a sampling arrangement as hereinbefore defined in a method of analysing an analyte present in a liquid to be sampled at a plurality of time points over a period of time.

DETAILED DESCRIPTION OF THE INVENTION

The present invention relates to a rack for holding sample vials. As used herein the term "rack" is used to refer to a tray or plate that is used to hold or support sample vials. The rack comprises a solid base, an upwardly extending wall around the perimeter of the base, a plurality of means for supporting a plurality of vials, each means for supporting one vial, and a means for draining liquid from the rack. Preferably the plurality of means for supporting a plurality of vials is located in the vicinity of the walls. Thus, preferably the rack of the present invention has an open space in the centre of the base surrounded by the wall. The open space serves two functions. First, it provides space for the fluid lines to which, in use, the sample vials contained in the rack are connected. Second, it contains and directs any liquid that is spilled or leaked from the vials or from fluid lines connected to the vials and prevents the liquid from entering into the liquid chromatography device.

Since a function of the base is to contain any spilled or leaked liquid, the base is solid. As used herein the term "solid base" is used to refer to an impermeable base which liquids cannot pass through. The base does not therefore contain any holes or apertures. Preferably the base also has a smooth surface, e.g. is dent free, so that any liquid present in the base can flow and cannot pool or collect in certain areas of the base. In some racks the base is essentially planar, i.e. flat. In other racks the base is concave when viewed from above. The concave shape of the base may assist in draining liquid out of the rack.

The base may be formed in any geometric or non-geometric shape. Preferably, however, the base is rectangular or square in shape and still more preferably rectangular in shape. The base of the rack can range in length from around 5 cm up to around 30 cm or more. Preferably the base is about 5 to 10 cm in length and more preferably 7.5 to 9 cm in length, e.g. about 8.5 cm in length. Preferably the base is about 10 to 15 cm wide and more preferably 12 to 14 cm wide, e.g. about 12.5 cm wide.

The rack of the present invention comprises an upwardly extending wall around the perimeter of the base. The wall is therefore formed at the edge or outside of the base. The solid base and wall preferably define an open space in the centre of the base. The wall prevents liquid present in the base from spilling or leaking into the liquid chromatography device. Preferably the wall extends around substantially the entirety of the perimeter of the base. As explained below in more detail, however, preferably the wall comprises an opening to allow liquid present in the base to drain therefrom.

Preferably the wall has a height of 1 to 3 cm and more preferably 1.5 to 2.8 cm, e.g. about 2.5 cm. Preferably the wall has a depth of 1.5 to 2.5 cm and more preferably 1.8 to 2.3 cm, e.g. about 2.1 cm.

In preferred racks of the invention, the plurality of means for supporting a plurality of vials is formed in the wall. Preferably the plurality of means for supporting a plurality of vials is formed in the wall along two, preferably opposing, sides of the solid base. Preferably the plurality of means for supporting a plurality of vials is regularly spaced, i.e. forms a regular pattern or array. This means that, in use, the vials are regularly spaced apart which makes automating sampling from the vials much easier.

As set out above, each means for supporting a vial supports one vial. The total number of means for supporting vials present in the rack depends on its size and on the size and design of the means for supporting. Preferably the rack of the present invention comprises a means for supporting 1 to 30 vials, more preferably 6 to 16 vials and still more preferably 8 to 12 vials.

In preferred racks of the present invention the plurality of means for supporting a plurality of vials is one or more cavities formed in the wall, each cavity being configured to receive one vial. Preferably the cavities are configured to snugly receive one vial. This means that once a vial is put in place in the rack it is held in position. This ensures that the vial is properly positioned for sampling by the liquid chromatography device.

Although it can be envisaged that cavities may be formed by, e.g. providing arms on the interior of the wall, in preferred racks of the invention the cavities are formed entirely within the wall. Preferably the cavities are formed as cut-outs or cut-aways from the wall. Preferably therefore, when in use, the vials are supported entirely or substantially entirely within the wall of the rack. Thus when viewed from above, the cross section of the cavity lies entirely within the cross section of wall. Nevertheless, in some embodiments, when in use, the vials are partially supported within the wall of the rack.

An important function of the cavities is that they hold the vial in a set position. Hence since sample vials are generally cylindrical in shape, preferred cavities have a fully or partially circular cross section (when viewed from above). In particularly preferred racks of the present invention, cavities have a partially circular cross section. Particularly preferably the cross section is 75 to 95% of a fully circular cross section. Preferably the cavities have a fully or partially circular cross section having a diameter in the range 1.0 to 1.8 cm and more preferably about 1.5 cm.

In preferred racks of the present invention, the cavities further comprise a slot in the wall connecting the cavity to the open space in the centre of said base. It is this slot which interrupts the circular cross section and creates the partial cross section of preferred cavities of the rack. The presence of the slot is advantageous as it provides space for the inlet and outlets of the vials which, in use, are present in the cavities and also provides space for the fluid lines that are connected to the inlets and outlets. Additionally, the slot may function as a channel by which any liquid that leaks from the vials and/or fluid is drained into the base.

A further essential feature of the rack of the present invention is a means for draining liquid from the base. This is important because the rack is located inside the liquid chromatography device in use and it is critical to prevent any liquid that leaks from the vials or fluid lines entering into the electronic circuitry of the device where it could cause significant damage. In preferred racks of the invention the means for draining liquid comprises a conduit connected to the base via an opening in the wall. The opening may comprise a gap in the wall or an aperture in the wall but is preferably a gap in the wall. Thus, at the base where the conduit is connected the perimeter wall is absent and instead a conduit is present. Preferably the conduit is downwardly sloping and extends below the plane of the base. Preferably the conduit is a walled channel. Alternatively the conduit may be a tube.

The rack of the present invention may optionally comprise one or more restraining bands. Preferably the restraining bands are flexible, e.g. elastic. The function of the restraining band is to prevent the fluid lines from lifting vials out of the rack during use. Preferably the band is fixed to the exterior of two opposing walls of the rack, particularly preferably the walls in which the plurality of means for supporting a plurality of vials is formed. In use, the band is preferably placed over the outlet (or inlet) of a plurality of vials thereby holding them in place in the rack.

The rack of the present invention may be formed of any inert material. Preferably, however, the rack comprises polyethylene, e.g. a high molecular weight polyethylene such as PE500. Racks of the appropriate shape may be formed by conventional methods, e.g. injection moulding.

The rack of the present invention is preferably for use in a sampling arrangement for a liquid chromatography device. As used herein the term sampling arrangement refers to a set up that provides a supply of samples to a liquid chromatography device such that the device can obtain an aliquot of each sample. A preferred sampling arrangement is automated. A further preferred sampling arrangement provides a continuous supply of liquid to be sampled.

The sampling arrangement of the present invention comprises a rack as hereinbefore defined. More preferably the sampling arrangement comprises:
(i) a rack as hereinbefore defined;
(ii) a plurality of sample vials supported by a plurality of means for supporting a plurality of vials, each vial being supported by one means and each vial comprising an inlet and an outlet;
(iii) at least one vessel comprising a liquid to be sampled;
(iv) inlet fluid lines connecting said vessel to said inlet of at least one vial;
(v) outlet fluid lines connecting said outlet of said vial to said vessel; and
(vi) a pump for pumping liquid from said vessel to said vial and from said vial to said vessel via said inlet and outlet fluid lines.

The at least one vessel can be any vessel or container which is suitable for holding reaction media, dissolution media, etc. to be monitored, such as conical flasks, round flasks, dissolution pots, test tubes, etc., and can be made of any suitable material for the purpose of holding the media being monitored, e.g. glass, plastic, ceramic, metal, etc.

In a preferred sampling arrangement the inlet and outlet of each of the vials is at opposing ends of the vial. In this case the means for supporting it, e.g. cavity, preferably further comprises a slot as hereinbefore defined to accommodate the inlets and outlets. Sample vials with such outlets, sometimes referred to as flow-through vials, are commercially available, e.g. from Gilson (p/n ACP 1040).

Preferably each of the vials has a height of 2.5 to 3.5 cm and more preferably 2.0 to 2.5 cm, e.g. about 2.2 cm. Preferably each of the vials has a circular cross section. Preferably each of the vials has a volume of 1 to 4 ml and more preferably 1.5 to 3 ml, e.g. about 2 ml. Preferably each of the vials has a screw cap. Preferably each of the vials is sealed with a septum.

As described above in relation to the rack, the open space of the rack preferably provides accommodation for the fluid lines. Thus, in a preferred sampling arrangement the fluid lines connecting the at least one vessel and the vials are located in the open space of the rack. The location of the fluid lines in this space prevents the lines from hindering the means for obtaining sample, e.g. the injection arm, of the liquid chromatography device. The fluid lines may be made of any inert material, e.g. PTFE or PVC. Suitable fluid lines are commercially available.

The sampling arrangement of the present invention may comprise one or more vessels. The sampling arrangement may comprise fewer vessels than vials. In this type of arrangement, each vessel is connected to a plurality of vials, i.e. replicate samples from the same vessel are obtained. A number of different possible configurations are possible.

Preferably, however, the arrangement comprises as many vessels as vials (i.e. a corresponding number of vessels and vials), with each vial being connected to a separate vessel via fluid lines. Preferably therefore the sampling arrangement comprises 1 to 30 vessels, more preferably 6 to 16 vessels, and still more preferably 8 to 12 vessels. Particularly preferably the sampling arrangement comprises a first set of, e.g. six, vessels and a second set of, e.g. six, vessels, with each vessel connected to a separate vial via fluid lines. Still more preferably each of the first and second set of vessels represents a set of replicate experiments. Yet more preferably a first set of vessels is connected via said fluid lines to a first group of a corresponding number of vials and a second set of vessels is connected via said fluid lines to a second group of a corresponding number of vials. An advantage of the sampling arrangement of the present invention is that replicate samples from multiple sets of vessels are simultaneously obtained and analysed.

In the sampling arrangement of the present invention, the pump may pump continuously (continuous flow arrangement) or at intervals (stop flow arrangement). When the pump pumps continuously, liquid continuously flows through the sampling arrangement from the vessel(s). When the pump pumps at intervals, the pump is configured to start pumping shortly before each sampling time point. This ensures that the sample in the vials is refreshed. Thus, the vials present in the sampling arrangement always comprise liquid to be sampled representative of the current sampling point in time. This is highly advantageous since it enables the progress of reactions, tests and studies, preferably in replicate, to be monitored over a period of time. In a particularly preferred sampling arrangement of the present invention, the pump continuously pumps sample from said vessel(s) to the vials via the fluid lines. Preferably the pump which pumps sample from the vessel(s) to the vials is a peristaltic pump. Suitable pumps are commercially available, e.g. from Watson Marlow.

The rack and sampling arrangement of the present invention are particularly suited for use in a liquid chromatography apparatus. The apparatus comprises a sampling arrangement as hereinbefore defined and a liquid chromatography device. The sampling arrangement hereinbefore described provides a supply, preferably a continuous supply, of samples that the liquid chromatography device analyses. The apparatus of the present invention therefore preferably provides online analysis and monitoring.

The liquid chromatography device may be any conventional device. Preferably the liquid chromatography device comprises:
a column and a mobile phase for separating analytes present in a liquid to be sampled;
a means for removing an aliquot of sample from each vial and introducing it into the column;
a pump for pumping the sample through the column; and
a detector for detecting analyte present in the outflow of the column.

A preferred device further comprises a shuttle tray for holding the sampling arrangement in position in the liquid chromatography device relative to said means for removing an aliquot of sample so that a sample may be removed from each vial. In a preferred device the means for removing an aliquot of sample from each vial removes an aliquot from each vial according to a predetermined pattern. The pattern determines when an aliquot is removed from each vial and in what order the samples are taken from the vials. The means is controlled by a programme that is a part of the liquid chromatography device and is conventional in the art.

In a preferred device of the present invention the means for removing an aliquot of sample comprises a moveable arm. Preferably this arm can move into the appropriate position to remove an aliquot sample from each vial in the rack of the sampling arrangement when the rack is in place in the liquid chromatography device. The arm preferably can also move into the appropriate position to inject the aliquot of sample into the column. Alternatively or additionally the arm may move into an appropriate position to inject the aliquot of sample into a dilution unit wherein the aliquot is diluted. In this case the dilution unit then introduces the resulting diluted aliquot into the column.

Preferably the means for removing an aliquot of sample comprises a needle and still more preferably a steel needle. Preferably the aliquot comprises 1 to 100 µl and still more preferably 1 to 50 µl of liquid. Still more preferably the means for removing an aliquot of sample does not comprise a punch pin for piercing the vial septum. This is advantageous because punch pins introduce large holes into septa from which leaks are inclined to occur. In contrast the smaller holes created by steel needles tend to reclose or at least reclose to the extent that little or no leakage occurs, therefore creating a better seal between needle and septum. In the event that liquid does spill or leak into the rack, however, it is advantageously drained by the means for draining liquid. Preferably this means extends outside the liquid chromatography device so that the liquid is conveyed away from the device and in particular its electronic circuitry. Nevertheless, preferred devices of the invention further comprise a leak sensor that is configured to switch off the, e.g. peristalitic, pump of the device in the event of a leak or spill.

A preferred apparatus of the present invention further comprises a second rack. This second rack may be a conventional rack or a rack of the present invention but is preferably a conventional rack. This rack supports a plurality of calibration samples, e.g. samples of the analyte being determined in different concentrations. These samples are used to generate a calibration plot.

As indicated above, the sampling arrangement of the present invention may be used in combination with any liquid chromatography device. Particularly preferably, however, the apparatus of the present invention comprises an ultra high performance liquid chromatography (UHPLC) device, such as an ACQUITY® UPLC® system available from Waters Corporation. Such devices have a high throughput, i.e. they enable a large number of samples to be analysed in a given period of time, and therefore they are particularly suited for use in combination with the sampling arrangement of the present invention which allows replicate samples from multiple vessels to be simultaneously and continuously obtained.

Preferably the liquid chromatography device comprises a column having particles having an average diameter of less than 2 µm and more preferably about 1.8 µm or 1.7 µm. Preferably the column has a diameter of 1.5 to 2.5 cm, e.g. about 2.1 cm. Preferably the column has a length of 3 to 15 cm and more preferably 3 to 5 cm. Typically the liquid chromatography device operates at a pressure in the range 50 to 100 MPa. Any conventional detector may be present in the device, e.g. a mass spectrometer, UV spectrometer, fluorescence detector, photodiode array or refractive index detector. Preferably, however, the detector is a UV spectrometer.

The sampling arrangement of the present invention enables replicate samples from multiple vessels to be simultaneously and continuously obtained. The sampling arrangement is therefore ideal for use in a method for analysing, preferably in replicate, an analyte present in a liquid to be sampled at a plurality of time points over a period of time. The method comprises:

(i) providing a continuous supply of sample of said liquid to a sampling arrangement, particularly a plurality of vials therein, as hereinbefore defined;

(ii) removing an aliquot of sample from said arrangement, particularly from each of the vials therein, at selected time points;

(iii) injecting said aliquot of said sample into a liquid chromatography device, e.g. a UHPLC device; and (iv) analysing said analyte.

In a preferred method of the invention the identity of the analyte is confirmed. In a further preferred method of the invention the quantity of the analyte is determined. The quantity of analyte is preferably determined using a calibration curve. A preferred method therefore further comprises removing an aliquot of sample from each of a number of calibration samples and plotting a calibration curve.

In the method of the invention one or more analytes may be analysed. For example, one, two, three or four analytes may be analysed.

The method of the present invention may be used to analyse a wide range of liquids, e.g. solutions and suspensions, and can generally be used in any process in which sampling, particularly online sampling, of liquid is required. Thus the liquid to be sampled may be any liquid from an ongoing or completed reaction, test or study e.g. from a synthetic chemical reaction, from dissolution testing of a formulation, from dissolution testing of a drug or from stability testing of a drug. A preferred use of the method is to monitor, e.g. synthetic, chemical reactions and the liquid to be sampled is a solution from the reaction mixture. A further preferred use of the method is to monitor dissolution of a formulation and the liquid to be sampled is a solution resulting from dissolution of a formulation.

DETAILED DESCRIPTION OF THE DRAWINGS

Figure 1:
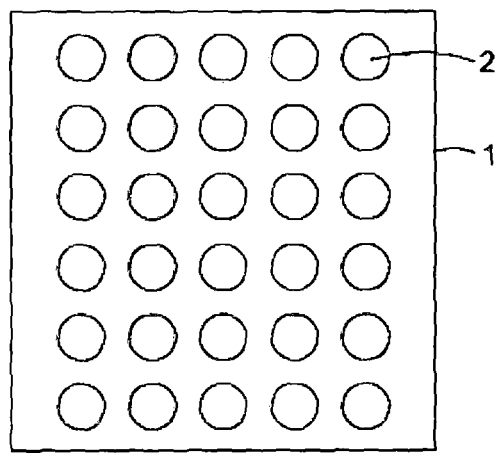
FIG. 1 shows a schematic of a conventional rack for holding sample vials in a liquid chromatography apparatus.

Referring to FIG. 1, it shows a schematic of a conventional rack 1 for holding sample vials in a liquid chromatography apparatus. The rack is rectangular in shape and comprises an array of cylindrical cavities 2 into which the sample vials can be placed. In the array the cavities are equally spaced apart and are distributed evenly across the surface of the rack. This ensures that the maximum number of cavities can be provided on a rack.

Figure 2A:
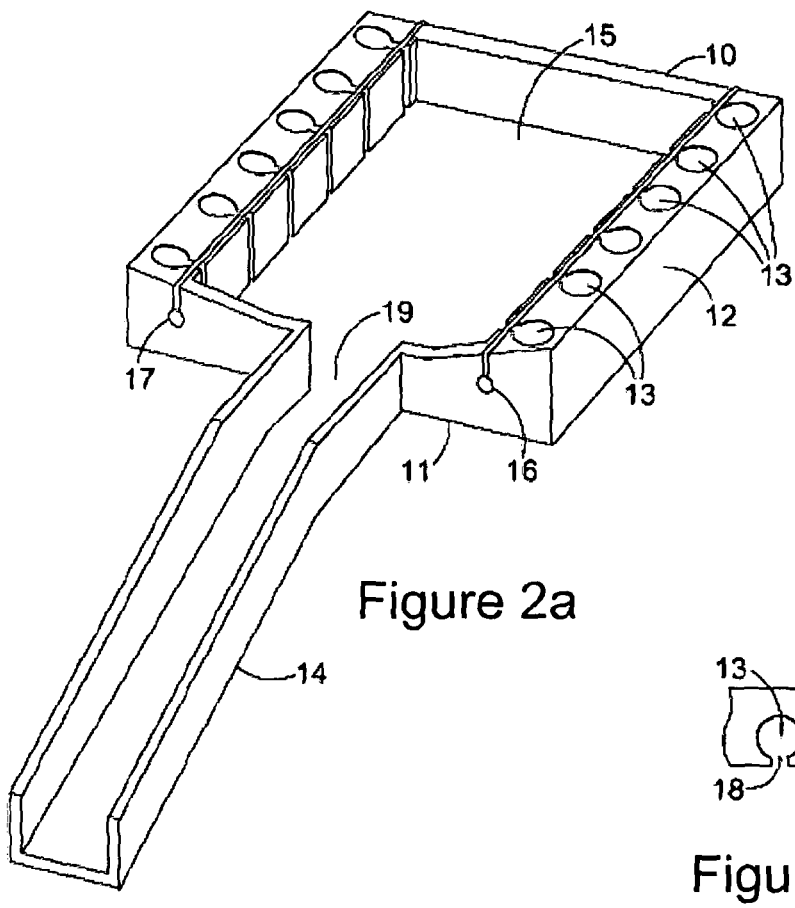
FIG. 2a shows a schematic of a rack of the present invention

Referring to FIG. 2a, it shows a schematic of a rack 10 of the present invention. It comprises a solid base 11, an upwardly extending wall 12 around the perimeter of the base, a plurality of means 13 for supporting a plurality of vials, each means supporting one vial, and a means 14 for draining liquid from the rack. The rack has an open or empty space 15 in the centre of the base which, in use, is occupied by fluid lines for connecting vials present in the rack to vessels. The open space also contains spilt or leaked liquid from one or more vials and/or fluid lines. The base is rectangular in shape and is 8.5 cm long by 12.5 cm wide. Although not shown the base may be concave, when viewed from above, to improve the draining of liquid out of the rack. Since the rack has a solid base and is shaped to ensure any liquid which could accumulate from leaks (from the vials or connecting lines) will drain out of the rack, the risk of liquid entering the liquid chromatography device is minimised. The wall 12 is around substantially the entirety of the perimeter of the base. The wall is 2.5 cm tall and 2.1 cm deep. The plurality of means 13 for supporting a plurality of vials are formed in the wall 12 and are regularly spaced apart in the wall. The plurality of means 13 for supporting a plurality of vials are present in the wall formed on two opposing sides of the solid base. In total the rack comprises means for supporting 12 vials. Two restraining bands 16, 17 are fixed on the exterior of wall 12 on opposing sides. In use, and as shown in FIG. 2a, these bands stretch over the cavities above the vial outlets and thereby prevent them from lifting from the tray.

Figure 2B:
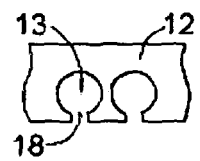
FIG. 2b shows a schematic of wall of a rack of the present invention.

As shown in FIG. 2a and in more detail in FIG. 2b the plurality of means for supporting a plurality of vials are cavities 13 formed in the wall. The cavity is formed entirely within the wall and is located towards the inside of the wall. Thus the centre of the cavity is closer to the inside of the wall than the outside. This means that the vials are supported entirely within the wall. The cavities are generally cylindrical in shape and have a partially circular cross section with a diameter of 1.5 cm. The cavities further comprise a slot 18 in the wall connecting the cavity to the open space 15 in the centre of the rack. This serves two functions. First it makes space for the vial inlets and outlets and the fluid lines connecting these to the vessels and second it provides a drain for any liquid that leaks out of the vials.

The rack of the present invention also comprises a means 14 for draining liquid. This is a conduit connected to the base via an opening 19 in the wall, specifically a gap in the wall. It is downwardly sloping and extends below the plane of the base. The conduit is typically a walled channel.

Figure 3A:
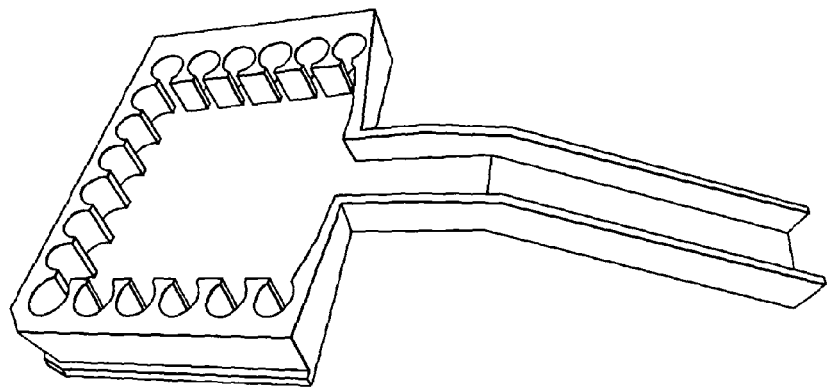
FIG. 3a is a photograph of a rack of the present invention.
Figure 3B:
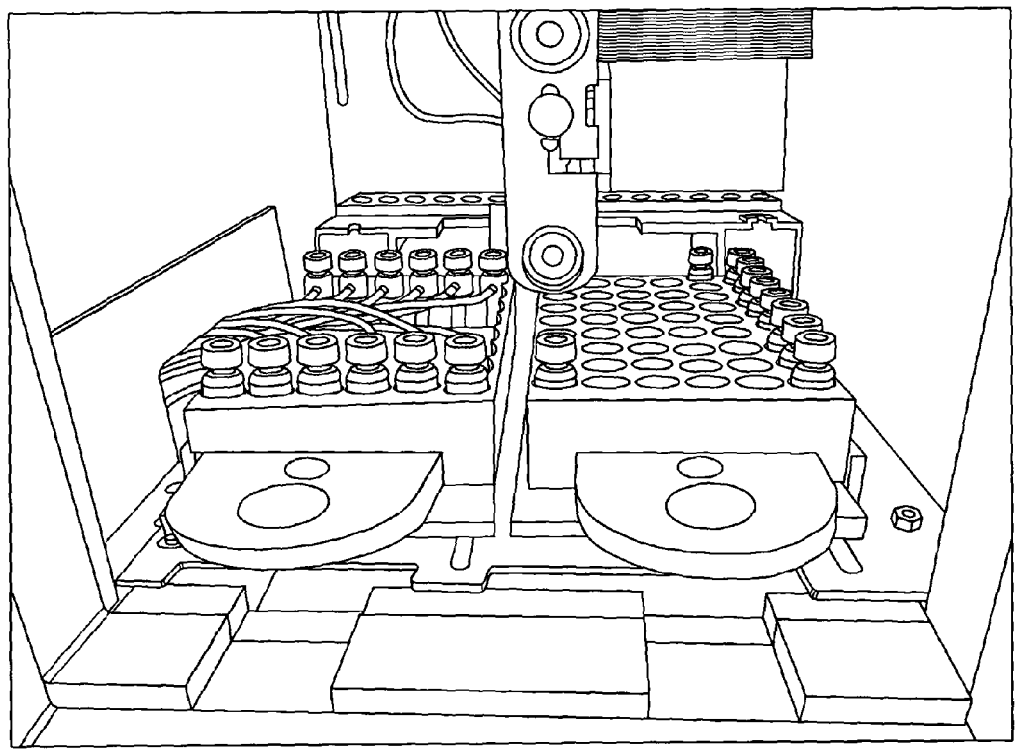
FIG. 3b is a photograph of a rack of the present invention and a conventional rack.

FIG. 3a shows a photograph of a rack of the present invention and FIG. 3b shows a photograph of a rack of the present invention and a conventional rack. In FIG. 3b some vials are present. Additionally FIG. 3b shows the fluid lines connected to the vials in the rack of the invention.

Figure 4A:
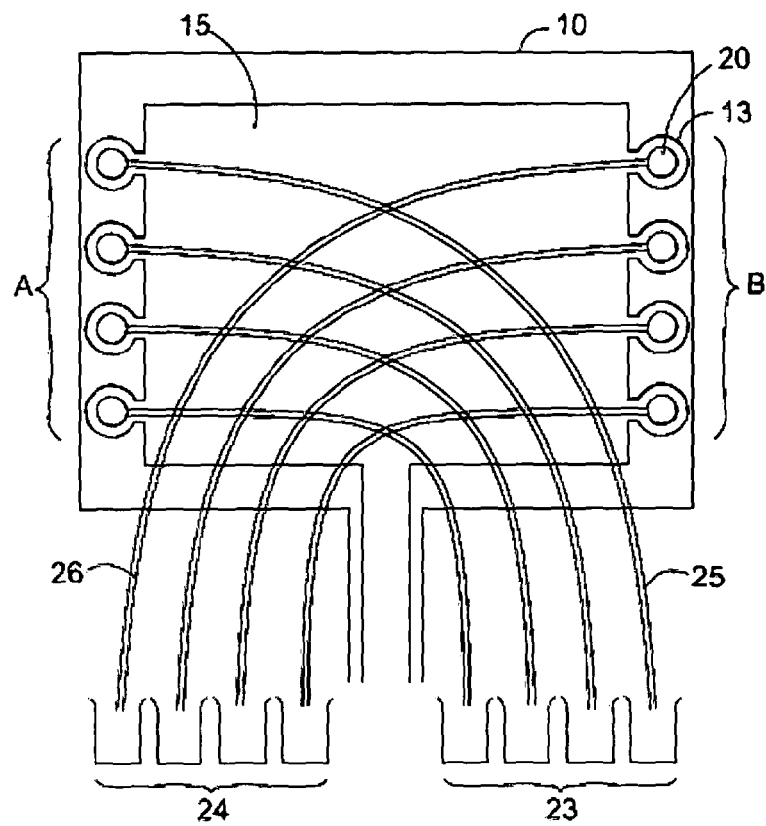
FIG. 4a is a schematic of a sampling arrangement of the present invention.
Figure 4B:
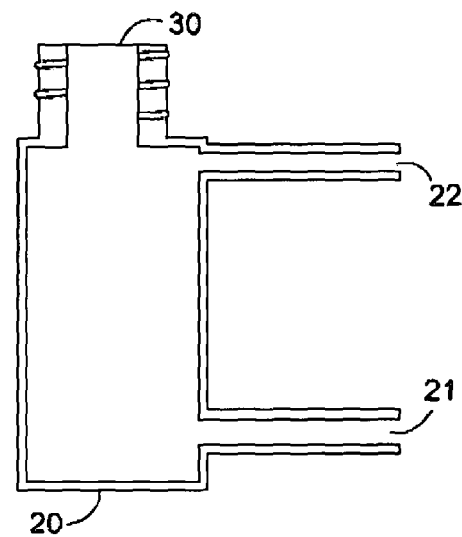
FIG. 4b is a schematic of a vial of the sampling arrangement of the present invention.

Referring to FIG. 4a, it shows a schematic of a sampling arrangement for a liquid chromatography device of the present invention. Referring to FIG. 4b it shows a vial 20 for use in the sampling arrangement. The sampling arrangement comprises a rack 10, a plurality of sample vials 20 supported by a plurality of means 13 for supporting a plurality of vials, each means supporting one vial and each vial comprising an inlet 21 and an outlet 22. The arrangement also comprises a first set of four vessels 23 and a second set of four vessels 24, each comprising a liquid to be sampled. The liquid in each of the vessels in the first set is identical, i.e. they represent replicate samples. The liquid in each of the vessels in the second set is identical, i.e. they represent another replicate set of examples. The plurality of sample vials 20 supported in the rack 10 are connected to the sets of vessels, 23, 24 by fluid lines 25, 26. The lines are located in the open space 15 of the rack 10.

Fluid lines 25 connect each vessel in the first set of vessels 23 to the inlet 21 and outlet 22 of each vial in a first group A of vials and fluid lines 26 connect each vessel in the second set of vessels 24 to the inlet 21 and outlet 22 of each vial in a second group B of vials. Thus, the first group of vials A represents a replicate set of experiments and the second group of vials B represents a replicate set of different experiments. An advantage of the arrangement of the present invention is that replicate samples of liquid from multiple vessels can be simultaneously obtained. Finally the arrangement also comprises a pump (not shown) for pumping liquid from the vessels to the vials and from the vials to the vessels via the fluid lines. The pump continuously pumps sample from the vessels to the vials. This means that the sample of liquid present in the vials at any given point in time is fresh, i.e. is representative of that time point.

As shown in FIG. 4b, the inlet 21 of the vials is towards the bottom of the vial and the outlet 22 is towards the top of the vial. This facilitates their connection to fluid lines 25, 26 whilst they are located in cavities 13. The vials are non-slit. Each of the vials is sealed with a septum 30. The vials have a height of 22.5 cm (to the neck) and a circular cross section having a diameter of 1.9 cm. The volume of the vials is 2 ml.

Figure 4C:
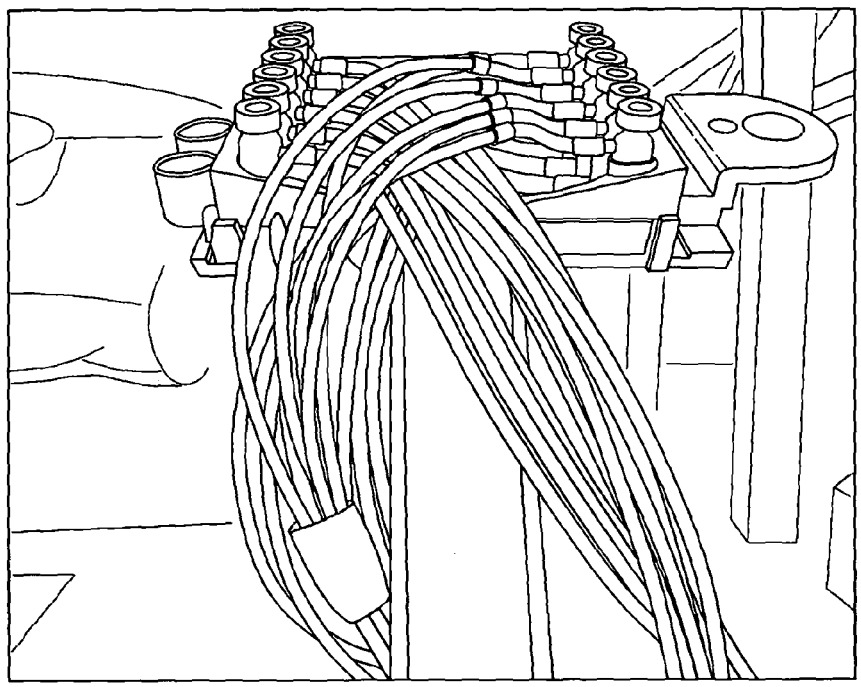
FIG. 4c is a photograph of a rack of the present invention connected to the lines of a sampling arrangement.
Figure 4D:
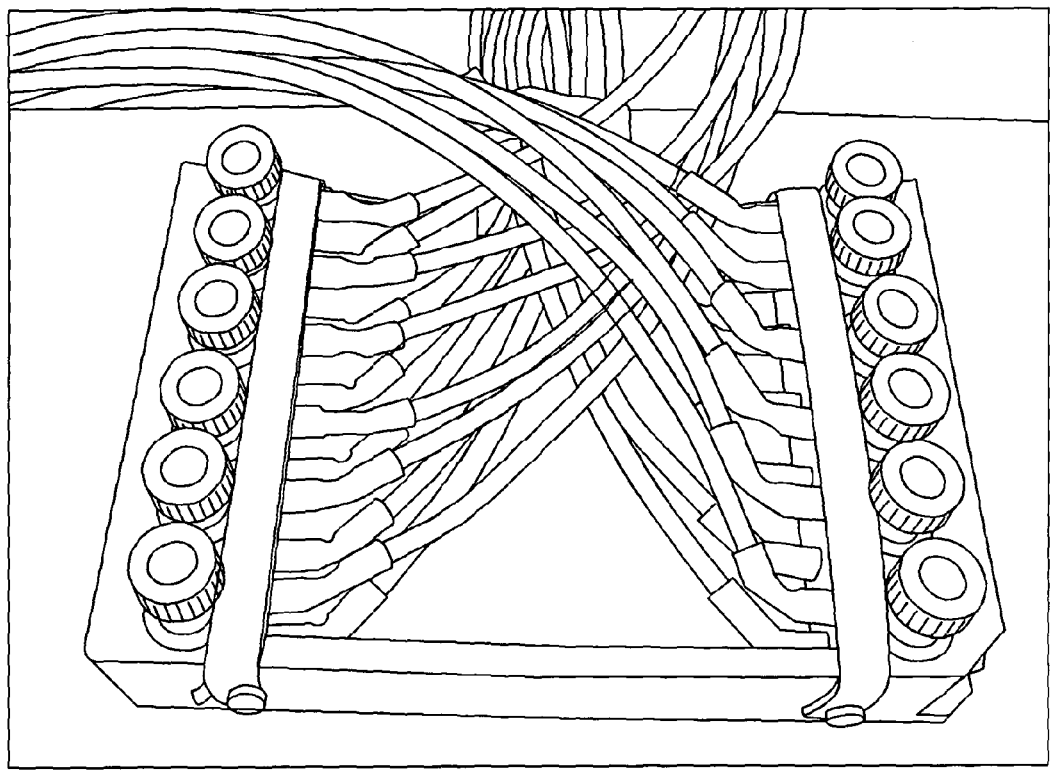
FIG. 4d is a photograph of a rack of the present invention, including its restraining bands, connected to the lines of a sampling arrangement.

FIG. 4c is a photograph of a rack of the present invention connected to the lines of a sampling arrangement and FIG. 4d is a photograph of a rack of the present invention showing the flexible restraining band used to hold the vials in place.

Figure 5:
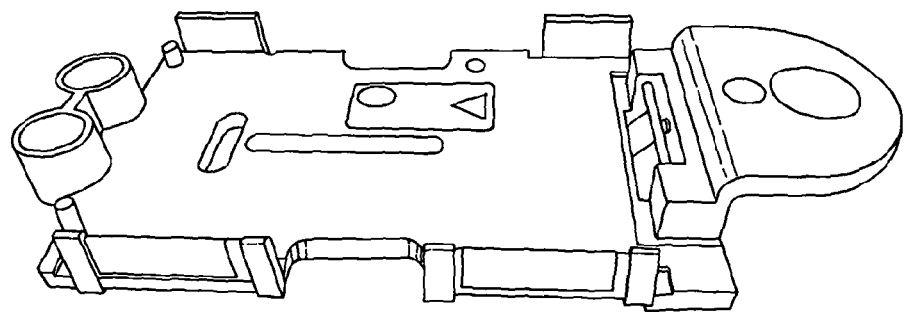
FIG. 5 is a photograph of a shuttle tray for use in a liquid chromatography device of present invention.

FIG. 5 is a photograph of a shuttle tray for use in a liquid chromatography device of the present invention. It accommodates the flow-through lines without any modification thereto. It is commercially available from Waters Corporation (p/n 205000542).

Figure 6A:
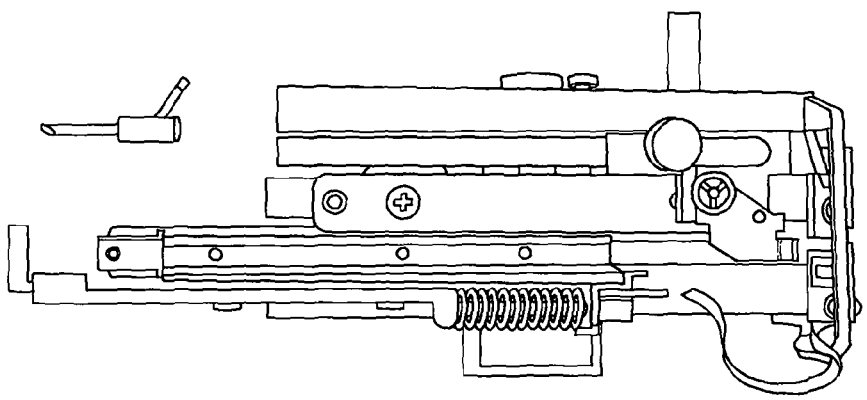
FIG. 6a is a photograph of a punch pin assembly.

FIG. 6a is a photograph of a punch pin which is a part of the assembly comprising the means for removing sample in the liquid chromatography device of the present invention.

Figure 6B:
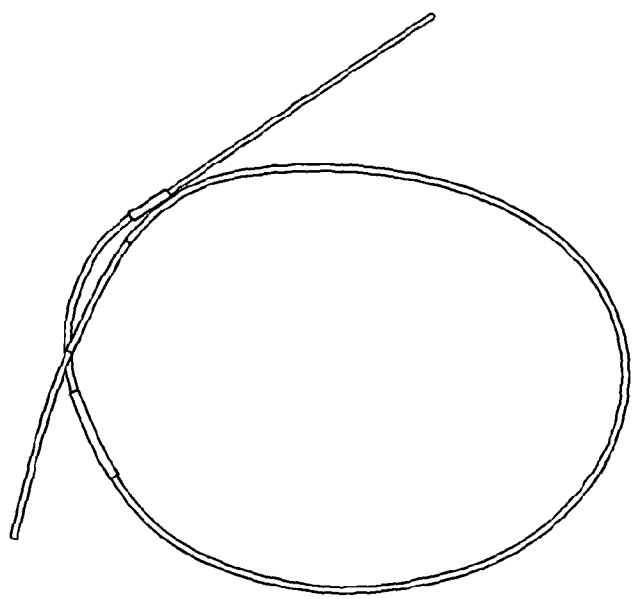
FIG. 6b is photograph of a means for removing sample in the liquid chromatography device of the present invention.

FIG. 6b is a photograph of a needle, particularly a steel needle, which is the means for removing sample in the liquid chromatography device. The needle is used to puncture the septum of sample vials without the pre-punching of a hole in the septum, e.g. by means of a punch pin, being necessary. The punch pin present in the needle carriage assembly of the liquid chromatography device has been shortened to 5 mm (from the standard length of 12 mm) so that, when fully descended, the punch pin is located just above the septa and therefore does not pierce the vial septa, which are then pierced by the stainless steel needle. These modifications were required to prevent leaking from the tops of vials after multiple injections. The needle removes an aliquot of sample from each vial according to a predetermined pattern controlled by a module in the liquid chromatography device.

Figure 7A:
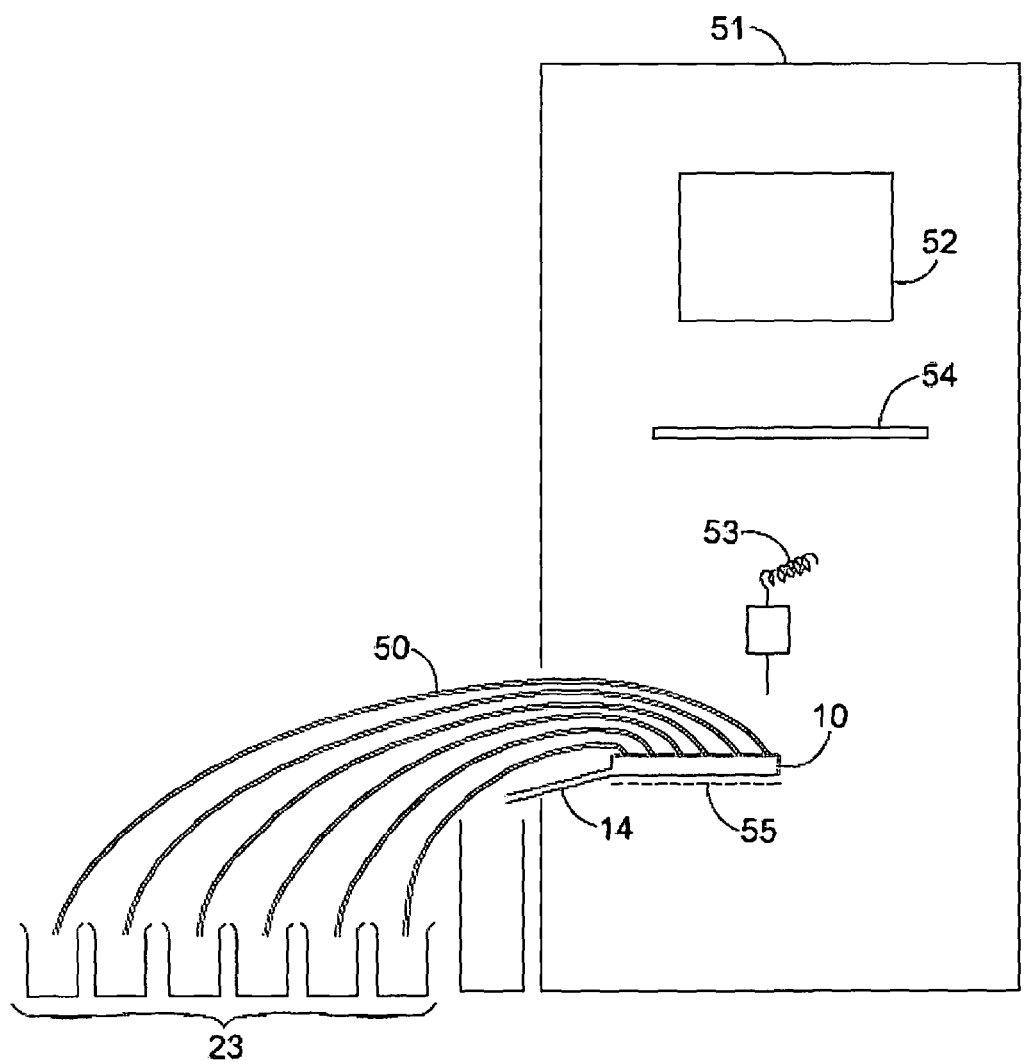
FIG. 7a is a schematic of a liquid chromatography apparatus of the present invention.

Referring to FIG. 7a, it shows a schematic of a liquid chromatography apparatus of the present invention. It comprises a sampling arrangement 50 and a liquid chromatography device 51. The liquid chromatography device comprises a column 54 and a mobile phase (not shown) for separating analytes present in the liquid to be sampled and a means 53 for removing an aliquot of sample from each vial and introducing it into the column. The apparatus also comprises a pump (not shown) for pumping the sample through the column and a detector 52 for detecting analyte present in the outflow of the column. A shuttle tray 55 holds the rack of the sampling arrangement 50 in position relative to said means 53 for removing an aliquot of sample so that a sample may be removed from each vial. The means 14 for draining liquid from said rack extends outside the liquid chromatography device.

Figure 7B:
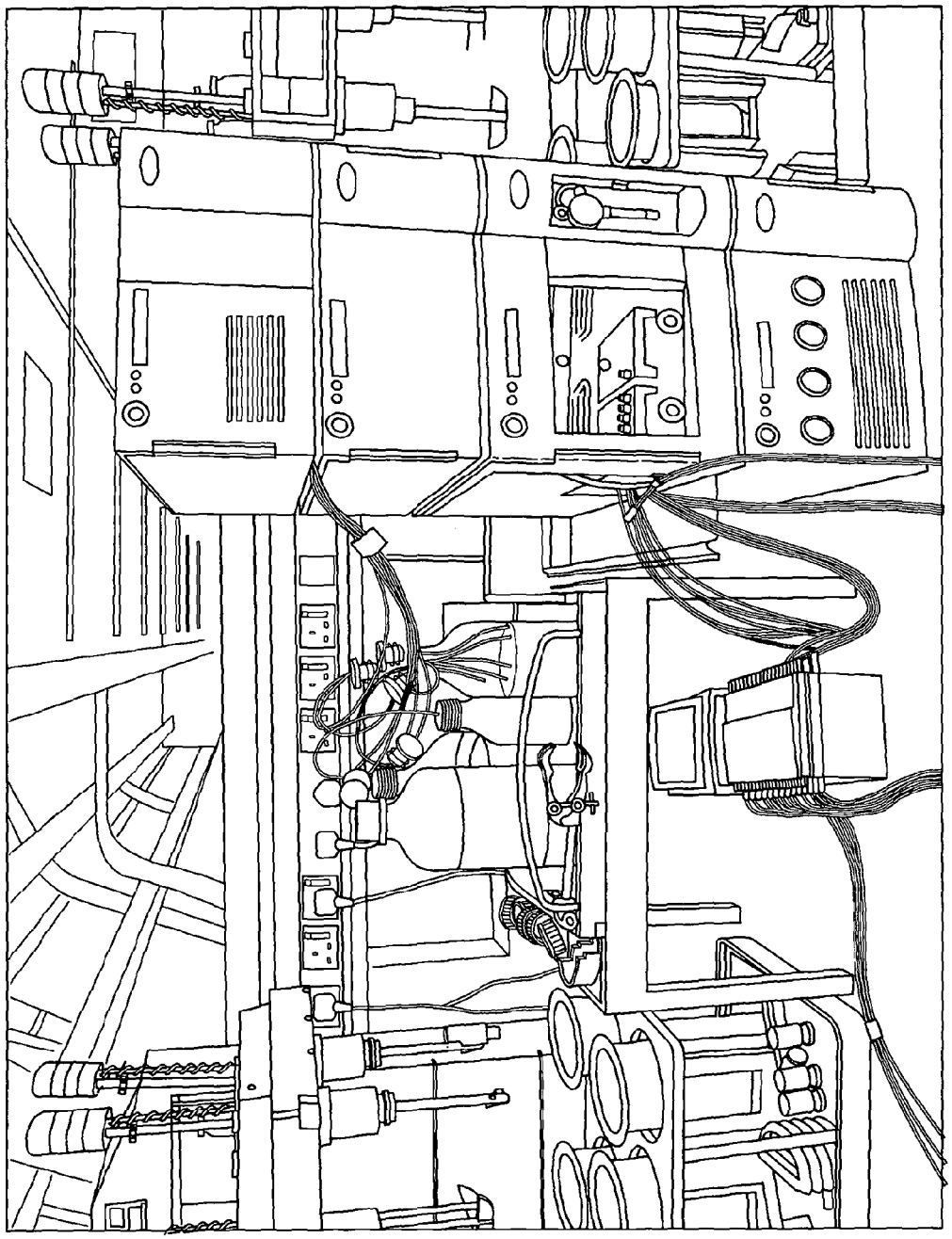
FIG. 7b is a photograph of a liquid chromatography apparatus of the present invention.

FIG. 7b is a photograph of a liquid chromatography apparatus of the present invention. The UHPLC system has been linked up to two sets of six vessels, namely dissolution pots, with tubing to 12 flow-through vials (via a peristaltic pump), to enable online UHPLC dissolution monitoring. The side panel of the liquid chromatography device has been removed to enable the 12 inlet/outlet lines from the two sets of six dissolution pots to feed into the flow-through vials in the rack. This is also shown in FIG. 3b.

EXAMPLES

An ACQUITY® UPLC® machine, commercially available from Waters Corporation, was modified in the following ways:

The side panel was removed from the Sample Manager (where the Sample organiser module would be connected)— to enable 12 lines from two sets of six vessels (one line per vessel), specifically dissolution pots, to feed into the flow-through vials in the rack.

The standard vial rack was replaced with a modified vial rack as hereinbefore described. This rack has a solid base and is shaped to ensure any liquid which could accumulate from leaks (from the vials or connecting lines) will drain out of the rack to a waste container and will not go into the Sample Manager or Binary Solvent Manager module. A flexible restraining band was attached to the modified rack to hold the vials securely in position to ensure they remain seated in the rack and are not pulled out or off-centre by the tubing lines connecting to the dissolution system. This is shown in FIG. 4d.

A new style shuttle tray, commercially available from Waters Corporation (p/n 205000542) is used in the apparatus. This was found to hold the modified rack more securely than the older style shuttle tray and also accommodates the flow-through lines without any modification to the shuttle tray being required.

The punch pin in the needle carriage assembly was shortened to 5 mm (from the standard length of 12 mm). The punch pin, when fully descended, is located just above the septa so that it does not pierce the vial septa, which are then pierced by a stainless steel needle. Non-pre-slit vials are used. These modifications were required to prevent leaking from the tops of vials after multiple injections—during a typical dissolution run of controlled-release formulations 16 injections per vial are performed.

An Empower template was generated to sample from each vial (and hence vessel, i.e. dissolution pot) every hour for 16 hours. Using a runtime varied from 3 minutes to 3 minutes 45 seconds (altered depending on the required injection volume) with the load ahead option enabled this allows analysis of samples taken from two sets of six vessels (each set contained in a separate dissolution bath) in twelve vials automatically overnight, with the required standard in vials in rack 2 of the Sample Manager. Optionally, the Empower software (or the sampling arrangement firmware) can be configured to calculate and control the exact timings of sampling from each vial.

Full details of modifications to set up system:

Removal of side panel on Sample Manager module (used for Sample Organiser).

Production of a new vial rack to hold twelve flow-through vials in sample rack 1 (in positions A1, B1, C1, D1, E1, F1 and A8, B8, C8, D8, E8, F8) with side chute (to direct any liquid away from the Sample Manager and Binary Solvent Manager modules).

The new rack is used with a new style shuttle tray (p/n 205000542).

The flow-through vials (Gilson p/n ACP1040) are connected via a peristaltic pump to two sets of six dissolution pots with a combination of rigid PTFE tubing (1/16" ID), flexible PVC tubing (2.79 mm ID) and Viton tubing (2.06 mm ID). These vials enable liquid to be pumped through tubing directly into the bottom of the vial and out at the top of the vial (e.g. Gilson flow-through vials (p/n ACP1040)).

The tubing is connected to dissolution cannula with 10 μm filters attached, which are placed into each dissolution pot (each pot has an inlet and an outlet cannula); the cannula are positioned upside down to prevent pressure build-up in the flow-through vials.

A suitable peristaltic pump (e.g. a Watson Marlow 205U pump) is operated at ≥5. 5 ml/min throughout the dissolution; the baths are set up and controlled independently, A flexible restraining band is attached to the modified vial rack to hold the vials securely in position to ensure that the vials are not pulled off-centre or upwards by the peristaltic tubing lines.

The lines and vials are labelled with the corresponding dissolution pot and bath to which they are connected.

The punch pin in the needle carriage assembly was shortened by 7 mm to 5 mm (from the standard length of 12 mm).

A stainless steel needle is fitted in the Sample Manager (required with the shortened punch pin, as the septa is no longer pierced by the punch pin—and is pierced only by the needle alone).

Non-pre-slit septa (commercially available from Waters Corporation, p/n 186002130) are used on the flow-through vials; these septa are typically used for five dissolution runs (~80 injections) before being replaced, with no leaks being observed for this level of usage.

An Empower template is used to sample from each vial (and hence dissolution pot) at the desired time points, e.g. every hour for 16 hours.

Standard vials are in sample rack 1 of the Sample Manager.

Figure 8A:
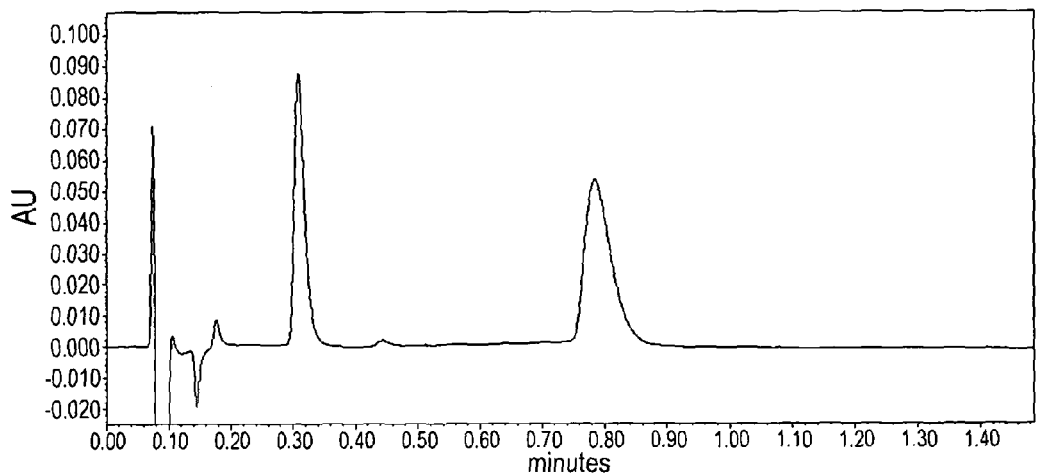
FIG. 8a shows a chromatogram produced by an apparatus of the present invention comprising a UHPLC device.

The modified UHPLC apparatus was used to generate the data shown in FIG. 8*a*. The chromatographic conditions used were:

Column: HSS T3 30×2.1 mm, 1.8 μm
Mobile phase: 92% 0.1% Formic Acid/Methanol
Flow rate: 1.2 ml/min
Column temperature: 30° C.

Figure 8B:
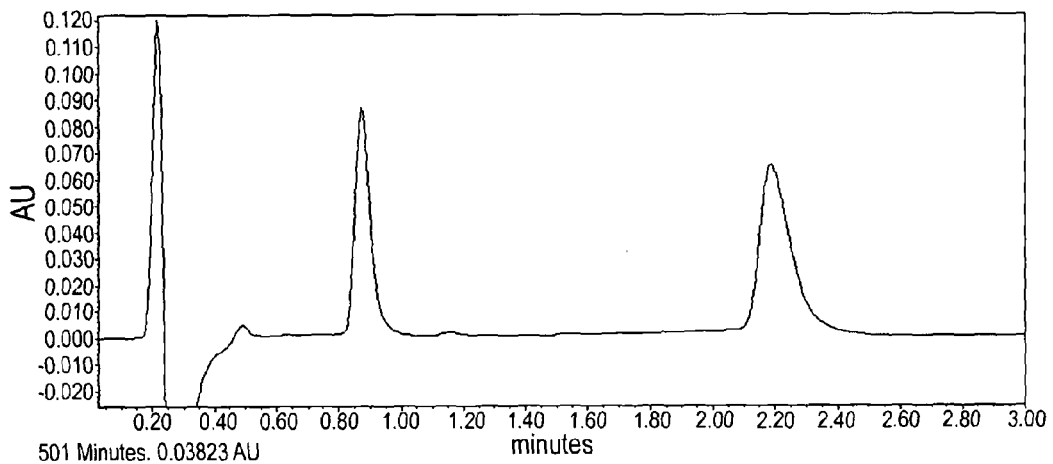
FIG. 8b shows a chromatogram produced by HPLC analysis of the same sample.
Figure 8C:
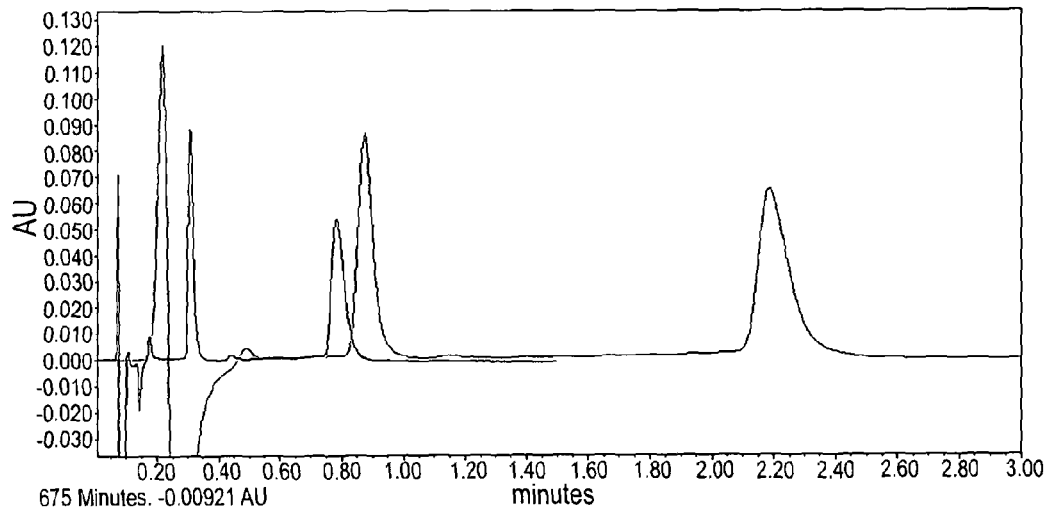
FIG. 8c compares the chromatograms of FIGS. 8a and 8b.
Figure 9:
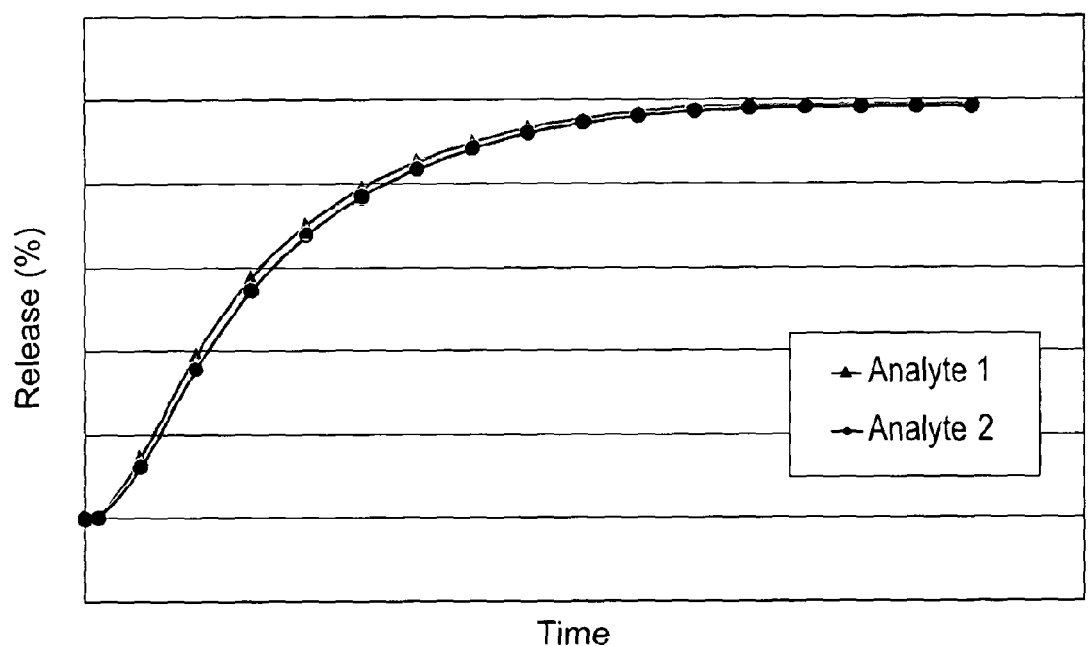
FIG. 9 shows the dissolution profile generated from chromatographic data taken at multiple time points according to a method of the invention.

FIG. 8*a* shows the chromatographic separation of two analytes in Simulated Gastric Fluid dissolution media. FIG. 8*b* shows the comparative HPLC chromatogram and FIG. 8*c* compares the UHPLC and HPLC runtimes and speed.

Advantages of the rack, sampling arrangement, liquid chromatography device and method of the present invention include:

- Capability to perform automated online reaction monitoring, e.g. dissolution studies, of multiple vessels with UHPLC monitoring.
- Capability to perform continuous online reaction monitoring, e.g. dissolution studies, of multiple vessels with UHPLC monitoring. The vessels may contain different reactions or replicate reactions.
- Speed: very short chromatographic runtimes and capable of monitoring multiple analytes using multiple vessels.
- Increased sensitivity: better detection of low strength products
- Increased separation: better separation of mixtures (e.g. may assist with separating complex Fassif/Fessif dissolution medias from active components).

The invention claimed is:

1. A rack for holding sample vials comprising:
   (i) a solid base that does not contain any holes or apertures;
   (ii) an upwardly extending wall around the perimeter of said base;
   (iii) a plurality of means for supporting a plurality of vials, each means for supporting one vial; and
   (iv) a means for draining liquid from said rack,
   wherein said means for draining liquid comprises a conduit connected to said base via an opening in the wall.

2. A rack as claimed in claim 1 having an open space in the centre of said base surrounded by said wall.

3. A rack as claimed in claim 1, wherein said plurality of means for supporting a plurality of vials is formed in said wall.

4. A rack as claimed in claim 1, wherein said plurality of means for supporting a plurality of vials is regularly spaced.

5. A rack as claimed in claim 1, wherein said plurality of means for supporting a plurality of vials is one or more cavities formed in said wall, each cavity being configured to receive one vial.

6. A rack as claimed in claim 3, wherein said vials are supported entirely within said wall.

7. A rack as claimed in claim 5, wherein said cavities have a full or partial circular cross section.

8. A rack as claimed in claim 5, wherein said cavities further comprise a slot in the wall connecting the cavity to the open space in the centre of said base.

9. A rack as claimed in claim 1, wherein said conduit is downwardly sloping and extends below the plane of said base.

10. A rack as claimed in claim 1, wherein said conduit is a walled channel.

11. A rack as claimed in claim 1, wherein said opening in the wall comprises a gap in the wall.

12. A sampling arrangement for a liquid chromatography device comprising:
    (i) a rack as defined in claim 1.

13. An arrangement as claimed in claim 12, further comprising:
    (ii) a plurality of sample vials supported by the plurality of means for supporting a plurality of vials, each vial supported by one means and each vial comprising an inlet and an outlet;
    (iii) at least one vessel comprising a liquid to be sampled;
    (iv) inlet fluid lines connecting said vessel to said inlet of at least one vial;
    (v) outlet fluid lines connecting said outlet of said vial to said vessel; and
    (vi) a pump for pumping liquid from said vessel to said vial and from said vial to said vessel via said inlet and outlet fluid lines.

14. An arrangement as claimed in claim 13, comprising a corresponding number of vessels to sample vials, each vessel being connected to one vial via said fluid lines.

15. An arrangement as claimed in claim 13, wherein each of said vials is sealed with a septum.

16. An arrangement as claimed in claim 13, wherein said fluid lines connecting said vessel and said vials are located in the open space of said rack.

17. An arrangement as claimed in claim 13, wherein a first set of vessels each comprise replicate samples of liquid to be simultaneously monitored.

18. An arrangement as claimed in claim 13, wherein a first set of vessels is connected via said fluid lines to a first group of a corresponding number of vials and wherein a second set of vessels is connected via said fluid lines to a second group of a corresponding number of vials.

19. An arrangement as claimed in claim 13, wherein said pump continuously pumps sample from said vessel(s) to said vials.

20. A liquid chromatography apparatus comprising:
    (i) a sampling arrangement as defined in claim 12; and
    (ii) a liquid chromatography device.

21. An apparatus as claimed in claim 20, wherein said liquid chromatography device comprises:
    a column and a mobile phase for separating analytes present in a liquid to be sampled;
    a means for removing an aliquot of sample from each vial and introducing it into said column;
    a pump for pumping said sample through said column; and
    a detector for detecting analyte present in the outflow of said column.

22. An apparatus as claimed in claim 21, further comprising a shuttle tray for holding said sampling arrangement in position relative to said means for removing an aliquot of sample so that a sample may be removed from each vial.

23. An apparatus as claimed in claim 21, wherein said means for removing an aliquot of sample comprises a needle.

24. An apparatus as claimed in claim 21, wherein said means for draining liquid from said rack extends outside the liquid chromatography device.

25. An apparatus as claimed in claim 21, wherein said liquid chromatography device is an ultra high performance liquid chromatography device.

26. A method for analysing an analyte present in a liquid to be sampled at a plurality of time points over a period of time comprising:

(i) providing a supply of sample of said liquid to a sampling arrangement as defined in claim 12;

(ii) removing an aliquot of sample from said arrangement at selected time points;

(iii) injecting said aliquot of said sample into a liquid chromatography device; and (iv) analysing said analyte.

27. A method as claimed in claim 26, wherein one or more analytes are analysed.

28. A method as claimed in claim 26, wherein the identity of the analyte is confirmed.

29. A method as claimed in claim 26, wherein the quantity of the analyte is determined.

30. A method as claimed in claim 26, wherein the liquid chromatography device is an ultra high performance liquid chromatography device.

31. A method as claimed in claim 26, wherein the liquid to be sampled is a solution formed by dissolution of a formulation.

\* \* \* \* \*